United States Patent
Nakazawa et al.

(10) Patent No.: US 7,662,984 B2
(45) Date of Patent: Feb. 16, 2010

(54) PREPARATION OF SI—SI BOND-BEARING COMPOUNDS

(75) Inventors: Hiroshi Nakazawa, Osaka (JP); Masumi Itazaki, Osaka (JP)

(73) Assignees: Public University Corporation Osaka City University, Osaka (JP); Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/261,917

(22) Filed: Oct. 30, 2008

(65) Prior Publication Data

US 2009/0112013 A1 Apr. 30, 2009

(30) Foreign Application Priority Data

Oct. 31, 2007 (JP) ............................. 2007-282965

(51) Int. Cl.
  *C07F 7/08* (2006.01)
(52) U.S. Cl. ..................... 556/430; 556/465; 556/466
(58) Field of Classification Search ................. 556/430, 556/465, 466
  See application file for complete search history.

(56) References Cited

FOREIGN PATENT DOCUMENTS

EP        0 671 487 A1      9/1995

OTHER PUBLICATIONS

Organometallics, 6, 1590 (1987).
Bull. Chem. Soc. Jpn., 68, 403, 1995.
J. Organomet. Chem., 593-594, 154, 2000.
J. Organomet. Chem., 279, C11, 1985.
J. Organomet. Chem., 521, 145, 1996.
Organosilicon Chemistry, VHC, Weinheim, p. 253, 1994.
P. Diversi et al., "Catalytic and stoichoimetric reactions of tertiary silanes with [Ir(Me)$_2$Cp*L] (CP*=$\eta^5$-C$_5$Me$_5$; L=PME$_3$, PMe$_2$Ph, PMe$_2$Ph$_2$, PPh$_3$) in the presence of one-electron oxidants. A unique case of Si—H, Si—C, Ir—C and P—F bonds one-step activation: crystal structure of [Ir(Ph)(SiPh$_2$F)Cp*(PMe$_3$)]," *Journal of Organometallic Chemistry*, 593-594, pp. 154-160 (2000).
K. A. Brown-Wensley, "Formation of Si—Si Bonds from Si—H Bonds in the Presence of Hydrosilation Catalysts," *Organometallics*, 6, 1590-1591 (1987).
H. Yamashita and M. Tanaka, "Transition Metal-Catalyzed Synthesis of Silicon Polymers," *Bull. Chem. Soc. Jpn.*, 68, 403-419 (1995).
C. Aitken and J. F. Harrod, "Polymerization of Primary Silanes to Linear Polysilanes Catalyzed by Titanocene Derivatives," *Journal of Organometallic Chemistry*, 279, C11-C13 (1985).
H. Brunner and K. Fisch, "Catalytic Hydrosilylation or Hydrogenation at One Coordination Site of [Cp'Fe(CO)(X)] Fragments," *Agnew. Chem. Int. Ed. Engl.*, 29, No. 10, 1131-1132 (1990).
D. L. Lichtenberger and A. Rai-Chaudhuri, "Electronic Structure of Transition Metal-Silicon Bonds. Valence Photoelectron Spectra of ($\eta$5-C$_5$H$_5$)Fe(CO)$_2$)L Complexes (L=SiCl$_3$, Si(CH$_3$)$_3$)," *J. Am. Chem. Soc.*, 113, 2923-2930 (1991).
C. L. Randolph and M. S. Wrighton, "Photochemical Reactions of ($\eta^5$-Pentamethylcyclopentadienyl)dicarbonyliron-Alkyl and -Silyl Complexes: Reversible Ethylene Insertion into an Iron-Silicon Bond and Implications for the Mechanism of Transition-Metal-Catalyzed Hydrosilation of Alkenes," *J. Am. Chem. Soc.*, 108, 3366-3374 (1986).

*Primary Examiner*—Elvis O Price
(74) *Attorney, Agent, or Firm*—Birch, Stewart, Kolasch & Birch, LLP

(57) ABSTRACT

Si—Si bond-bearing compounds are effectively prepared by irradiating with radiation or heating Si—H group-bearing silicon compounds in organic solvents in the presence of iron complex catalysts. The Si—Si bond-bearing compounds are useful as a base material in photoresist compositions, ceramic precursor compositions, and conductive compositions.

17 Claims, No Drawings

PREPARATION OF SI—SI BOND-BEARING COMPOUNDS

CROSS-REFERENCE TO RELATED APPLICATION

This non-provisional application claims priority under 35 U.S.C. §119(a) on Patent Application No. 2007-282965 filed in Japan on Oct. 31, 2007, the entire contents of which are hereby incorporated by reference.

TECHNICAL FIELD

This invention relates to a process for preparing silicon-containing compounds, and more particularly, to a process for preparing Si—Si bond-bearing compounds, typically disilanes, by irradiating with radiation or heating ≡Si—H group-bearing silicon compounds, typically monohydrosilanes, in organic solvents in the presence of iron complex catalysts.

BACKGROUND ART

Disilanes are useful base materials in photoresist compositions, ceramic precursor compositions, and electroconductive compositions, and particularly in photoresist compositions having oxygen plasma etching resistance.

In the prior art, disilanes are generally prepared through polycondensation of halosilanes in the presence of alkali metals such as lithium and sodium or reaction of halosilanes with alkali metal silicides such as silyllithium, provided that by-product disilanes formed during preparation of halosilanes by the direct process and derivatives thereof are excluded. These processes, however, involve hazards due to the use of alkali metals and are impossible, in principle, to produce disilanes having substituent groups capable of reacting with alkali metals.

It is also known to prepare disilanes by dehydrogenation condensation of hydrosilanes in the presence of noble metal catalysts. Being free from hazardous alkali metals, this process is of greater interest than the above halosilane processes. Rhodium, platinum, and iridium catalysts for use in such process are known from Organometallics, 6, 1590 (1987), Bull. Chem. Soc. Jpn., 68, 403, 1995, and J. Organomet. Chem., 593-594, 154, 2000, respectively. These catalysts are commercially less acceptable because of the expense of noble metals. Use of titanium catalysts is also reported in J. Organomet. Chem., 521, 145, 1996, J. Organomet. Chem., 279, C11, 1985, and Organosilicon Chemistry, VCH, Weinheim, p.253, 1994.

These prior art processes of forming Si—Si bonds through dehydrogenation condensation in the presence of noble metal catalysts or titanium catalysts start with dihydrosilanes or trihydrosilanes. Namely, the starting reactants must be silanes having at least two hydrogen atoms on a common silicon atom. For example, in the case of coupling of a primary or secondary silane with a lithium reagent such as BuLi in the presence of a titanium or Group 4 transition metal complex catalyst, a polysilane forms because a plurality of Si—H bonds are available as reaction sites. It is difficult to preferentially produce only the desired disilane.

The foregoing prior art processes fail to effect dehydrogenation condensation on monohydrosilanes, that is, silanes having one hydrogen atom on a silicon atom. Even when disilanes are produced, the amount of disilane produced does not exceed the amount of noble metal used as the catalyst. The processes are by no means economically acceptable.

DISCLOSURE OF THE INVENTION

An object of the invention is to provide a process for preparing Si—Si bond-bearing compounds, typically disilanes in high yields using Si—H group-bearing silicon compounds as the starting reactant.

The inventors have discovered that when a ≡Si—H group-bearing silicon compound is used as the starting reactant and irradiated with radiation and/or heated in an organic solvent in the presence of an iron complex as the catalyst, dehydrogenation of ≡Si—H group occurs to form ≡Si—Si≡ bond, so that a compound having a Si—Si bond is produced in high yields by an inexpensive simple process.

According to the invention, a process for preparing a Si—Si bond-bearing compound is provided, the process comprising the step of irradiating a Si—H group-bearing silicon compound with radiation or heating the compound, in an organic solvent in the presence of an iron complex catalyst.

In one embodiment, the Si—H group-bearing silicon compound is a monohydrosilane having the general formula (1):

$$R^1R^2R^3Si—H \qquad (1)$$

wherein $R^1$, $R^2$ and $R^3$ are monovalent organic groups, and the resulting Si—Si bond-bearing compound is a disilane having the general formula (2):

$$R^1R^2R^3Si—SiR^1R^2R^3 \qquad (2)$$

wherein $R^1$, $R^2$ and $R^3$ are as defined above. Preferably, monovalent organic groups of $R^1$, $R^2$ and $R^3$ are independently selected from among halo-substituted or unsubstituted alkyl, cycloalkyl, aryl, heterocyclic, aralkyl, alkoxy, aryloxy, alkenyl, alkynyl, ferrocenyl groups, and siloxane residues.

The preferred iron complex may be $(C_5H_5)Fe(CO)_2CH_3$, $(C_5H_5)Fe(CO)_2Si(CH_3)_3$, or $[C_5(CH_3)_5]Fe(CO)_2CH_3$. The preferred organic solvent may be a nitrogen-containing organic compound.

In a preferred embodiment, the Si—H group-bearing silicon compound is irradiated with electromagnetic wave having a shorter wavelength than the visible light or it is heated at a temperature of 50 to 150° C. Irradiation and/or heating causes the Si—H group-bearing silicon compound to undergo dehydrogenation condensation reaction.

BENEFITS OF THE INVENTION

By the process of the invention, Si—Si bond-bearing compounds are efficiently produced in an industrially advantageous manner. They are useful base materials in photoresist compositions, ceramic precursor compositions, and electroconductive compositions.

DESCRIPTION OF THE PREFERRED EMBODIMENT

Briefly stated, the process of the invention involves irradiating a ≡Si—H group-bearing silicon compound, typically a monohydrosilane with radiation and/or heating the compound, is in an organic solvent in the presence of an inexpensive iron complex catalyst, thereby producing a Si—Si bond-bearing compound, typically a disilane. The ≡Si—H group-bearing silicon compound used herein is desirably a monohydrosilane. Specifically, the ≡Si—H group-bearing silicon compound is desirably selected from monohydrosilanes having the general formula (1):

$$R^1R^2R^3Si—H \qquad (1)$$

wherein $R^1$, $R^2$ and $R^3$ are independently monovalent organic groups.

Suitable monovalent organic groups represented by $R^1$, $R^2$ and $R^3$ include halo-substituted (e.g., chloro or fluoro-substituted) or unsubstituted alkyl, cycloalkyl, aryl, heterocyclic, aralkyl, alkoxy, aryloxy, alkenyl, and alkynyl groups, preferably of 1 to 12 carbon atoms, more preferably 1 to 8 carbon atoms. Also included are siloxy and ferrocenyl groups.

Exemplary groups include methyl, ethyl, isopropyl, and t-butyl as exemplary alkyl groups; cyclohexyl as an exemplary cycloalkyl group; phenyl and naphthyl as exemplary aryl groups; pentafluorophenyl as an exemplary halo-substituted aryl group; benzyl as an exemplary aralkyl group; ethoxy and isopropoxy as exemplary alkoxy groups; phenoxy as an exemplary aryloxy group, and trimethylsiloxy as an exemplary siloxy group.

The catalyst used herein is an iron complex. The iron complex is a compound having at least one equivalent of ligand relative to iron within the molecule. In the iron complex, carbon, nitrogen, phosphorus, silicon or arsenic serves as electron donative ligands. These ligands need not have previously formed a complex with iron. An effective catalysis is achievable by introducing both an iron component and a ligand component in the reaction system such that the ligand component is at least one equivalent relative to iron.

When added to the reaction system, the form of iron component is not particularly limited. The iron component may be added in any form of organic salts, inorganic salts or complexes. The preferred ligands for the reaction include carbon, nitrogen, phosphorus, silicon and arsenic compounds, for example, cyclopentadienyl, alkyl, carbonyl, phosphine, phosphate, trialkylsilyl, and arsine compounds. More preferred ligands include methyl, carbonyl, (substituted) cyclopentadienyl, and trimethylsilyl. As such, preferred complex catalysts suitable for the reaction include cyclopentadienyl-dicarbonyl(methyl)iron (($C_2H_5$)Fe(CO)$_2$CH$_3$), cyclopentadienyl-dicarbonylCtrimethylsilyl)iron (($C_5H_5$)Fe(CO)$_2$Si(CH$_3$)$_3$), and [$C_5$(CH$_3$)$_5$]Fe(CO)$_2$CH$_3$. The catalyst may be used in a catalytic amount, specifically in a range of 0.5 to 0.0001 mole per mole of the organosilicon compound.

The reaction is performed in an organic solvent. The organic solvent used herein may be selected from ordinary solvents excluding ketone and analogous solvents susceptible to hydrosilylation and alcohol and analogous solvents containing active hydrogen. Inter alia, nitrogen-containing organic solvents such as dimethylformamide(DMF) and acetonitrile are most desirable. The amount of organic solvent used may be determined as appropriate, and preferably so as to give a concentration of 1 to 50% by weight, more preferably 5 to 20% by weight of the Si—H group-bearing silicon compound in the organic solvent.

With respect to reaction conditions, a temperature of at least 0° C., and preferably 25° C. to 150° C. may be employed. At room temperature, reaction may be effectively driven by irradiating the reaction system with radiation, especially electromagnetic wave having a shorter wavelength than the visible light, typically ultraviolet radiation. Also, reaction may be effectively driven by heating the reaction system at a temperature of 50° C. to 150° C. Irradiating the reaction system with radiation along with heating at 50° C. to 150° C. is also effective.

Specifically, the reaction may be carried out by heating the system at a temperature of 50° C. to 150° C., and preferably 60° C. to 120° C., or by irradiating the system with ultraviolet radiation having a shorter wavelength than the visible light, or both. For the UV exposure, a high-pressure mercury lamp capable of emission at wavelength 365 nm may be employed.

The reaction time is generally 0.1 to 500 hours, and especially 0.5 to 100 hours.

From the reaction mixture, the product may be readily isolated and purified by organochemical measures commonly used in the art, such as distillation and chromatography.

Through the above reaction where dehydrogenation of ≡Si—H group occurs and ≡Si—Si≡ bond is formed instead, the Si—H group-bearing silicon compound is converted to a Si—Si bond-bearing compound. Specifically, when a monohydrosilane having the general formula (1) is used, a disilane having the general formula (2) is produced.

$R^1R^2R^3Si$—H                    (1)

$R^1R^2R^3Si$—$SiR^1R^2R^3$                    (2)

Herein $R^1$, $R^2$ and $R^3$ are as defined above.

The process of the invention carries out catalytic dehydrogenation condensation of a ≡Si—H group-bearing silicon compound, enabling industrially advantageous formation of a Si—Si bond-bearing compound. By this process, disilanes can be efficiently produced from a wide variety of monohydrosilanes in an industrially advantageous manner. The disilanes thus produced are useful as a base material in s photoresist compositions, ceramic precursor compositions, and conductive compositions.

EXAMPLE

Examples of the invention are given below by way of illustration and not by way of limitation. The abbreviation Cp stands for cyclopentadienyl, Me for methyl, Ph for phenyl, Et for ethyl, and iPr for isopropyl. DMF is dimethylformamide.

Example 1 (Table 2, Run #1): Irradiation

A nitrogen-purged Schlenk tube was charged with 38 mg (0.2 mmol, 4 mol %) of iron complex CpFe(CO)$_2$Me, 681 mg (5 mmol) of dimethylphenylsilane, and 4.6 mL of DMF. The reaction mixture was irradiated with UV at room temperature for one hour, using a high-pressure mercury lamp model UVL-400HA (Riko Kagaku Sangyo K.K., 400 W, main emission wavelength 365 nm).

After the solvent was distilled off in reduced pressure, the product was purified by silica gel column chromatography (dichloromethane:hexane=1:3), yielding tetramethyldiphenyldisilane.

Gas chromatography(GC) analysis demonstrated a conversion of dimethylphenylsilane equal to 100%, identifying 676 mg (2.5 mmol) of 1,1,2,2-tetramethyl-1,2-diphenyldisilane (abbreviated as PhMe$_2$Si—SiMe$_2$Ph).

Example 2 (Table 1): Heating (No Irradiation)

Dimethylphenylsilane (abbreviated as PhMe$_2$SiH) in DMF with 4 mol % of CpFe(CO)$_2$Me catalyst was heated at different temperatures as shown in Table 1 for 12 hours, producing the disilane (PhMe$_2$Si—SiMe$_2$Ph). The percent yield of disilane was determined.

The results are shown in Table 1. The relation of product yield to reaction temperature is such that at a lower reaction temperature (50° C.), reaction does not effectively proceed, resulting in reduced yields. At too high temperatures (e.g., 120° C. and 153° C., the boiling point of DMF), the iron complex appeared to be decomposed, resulting in reduced yields.

TABLE 1

(Fe cat. = CpFe(CO)$_2$Me)

| Run No. | Temperature (° C.) | Yield (%) |
|---|---|---|
| 1 | 50 | 27 |
| 2 | 80 | 75 |
| 3 | 120 | 30 |
| 4 | 153 | 24 |

Examples 3 to 13 (Table 2, Run #2 to #12)

Solutions of eleven monohydrosilanes (other than dimethylphenylsilane) in DMF with 4 mol % of CpFe(CO)$_2$Me iron complex catalyst were prepared as shown in Table 2 and irradiated with ultraviolet radiation under a high-pressure mercury lamp. Reaction was carried out for varying times under the same conditions as in Example 1 except that the amount of iron complex catalyst was changed to 0.5 mmol only when the hydrosilane reactant was triphenylsilane. The results are shown in Table 2 together with the result of Example 1.

TABLE 2

| Run No. | Hydrosilane | Time (hr) | Yield (%) |
|---|---|---|---|
| 1 | PhMe$_2$SiH | 1 | 100 |
| 2 | (C$_6$F$_5$)Me$_2$SiH | 12 | 86 |
| 3 | Ph$_2$MeSiH | 24 | 99 |
| 4 | Ph$_3$SiH | 48 | 95 |
| 5 | (PhCH$_2$)Me$_2$SiH | 24 | 95 |
| 6 | (PhCH$_2$)PhMeSiH | 24 | 60 |
| 7 | (CH$_2$=CH)PhMeSiH | 24 | 91 |
| 8 | Et$_3$SiH | 12 | 51 |
| 9 | ($^i$PrO)PhMeSiH | 24 | 69 |
| 10 | (Me$_3$SiO)Me$_2$SiH | 12 | 65 |
| 11 | (Me$_3$SiO)$_2$MeSiH | 12 | 50 |
| 12 | CpFe(C$_5$H$_4$Me$_2$SiH) | 24 | 92 |

It is evident from Table 2 that corresponding disilanes were produced in high yields of 50% to 100%.

Japanese Patent Application No. 2007-282965 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A process for preparing a Si—Si bond-bearing compound, comprising irradiating with radiation or heating a Si—H group-bearing silicon compound in an organic solvent in the presence of a catalyst consisting essentially of an iron complex catalyst.

2. The process of claim 1 wherein said Si—H group-bearing silicon compound is a monohydrosilane having the general formula (1):

$$R^1R^2R^3Si\text{—}H \qquad (1)$$

wherein R$^1$, R$^2$ and R3 are monovalent organic groups, and the resulting Si—Si bond-bearing compound is a disilane having the general formula (2):

$$R^1R^2R^3Si\text{—}SiR^1R^2R^3 \qquad (2)$$

wherein R$^1$, R$^2$ and R$^3$ are as defined above.

3. The process of claim 2 wherein R$^1$, R$^2$ and R$^3$ are monovalent organic groups which are independently selected from the class consisting of halo-substituted or unsubstituted alkyl, cycloalkyl, aryl, heterocyclic, aralkyl, alkoxy, aryloxy, alkenyl, alkynyl, ferrocenyl groups, and siloxane residues.

4. The process of claim 1 wherein the iron complex is (C$_5$H$_5$)Fe(CO)$_2$CH$_3$, (C$_5$H$_5$)Fe(CO)$_2$Si(CH$_3$)$_3$, or [C$_5$(CH$_3$)$_5$]Fe(CO)$_2$CH$_3$.

5. The process of claim 1 wherein the organic solvent is a nitrogen-containing organic compound.

6. The process of claim 1 wherein the step of irradiating with radiation or heating includes irradiating with electromagnetic wave having a shorter wavelength than the visible light or heating at a temperature of 50 to 150° C., or both, for causing the Si—H group-bearing silicon compound to react.

7. A process for preparing a Si—Si bond-bearing compound, comprising irradiating with radiation or heating a Si—H group-bearing silicon compound in an organic solvent in the presence of an iron complex catalyst selected from the group consisting of (C$_5$H$_5$)Fe(CO)$_2$CH$_3$, (C$_5$H$_5$)Fe(CO)$_2$Si(CH$_3$)$_3$, and [C$_5$(CH$_3$)$_5$]Fe(CO)$_2$CH$_3$.

8. The process of claim 7, wherein said Si—H group-bearing silicon compound is a monohydrosilane having the general formula (1):

$$R^1R^2R^3Si\text{—}H \qquad (1)$$

wherein R$^1$, R$^2$ and R$^3$ are monovalent organic groups, and the resulting Si—Si bond-bearing compound is a disilane having the general formula (2):

$$R^1R^2R^3Si\text{—}SiR^1R^2R^3 \qquad (2)$$

wherein R$^1$, R$^2$ and R$^3$ are as defined above.

9. The process of claim 8, wherein R$^1$, R$^2$ and R$^3$ are monovalent organic groups which are independently selected from the class consisting of halo-substituted or unsubstituted alkyl, cycloalkyl, aryl, heterocyclic, aralkyl, alkoxy, aryloxy, alkenyl, alkynyl, ferrocenyl groups, and siloxane residues.

10. The process of claim 7, wherein the organic solvent is a nitrogen-containing organic compound.

11. The process of claim 7, wherein the step of irradiating with radiation or heating includes irradiating with electromagnetic wave having a shorter wavelength than the visible light or heating at a temperature of 50 to 150° C., or both, for causing the Si—H group-bearing silicon compound to react.

12. A process for preparing a Si—Si bond-bearing compound, comprising irradiating with radiation or heating a Si—H group-bearing silicon compound in an organic solvent in the presence of an iron complex catalyst without an iridium catalyst.

13. The process of claim 12, wherein said Si—H group-bearing silicon compound is a monohydrosilane having the general formula (1):

$$R^1R^2R^3Si\text{—}H \qquad (1)$$

wherein R$^1$, R$^2$ and R$^3$ are monovalent organic groups, and the resulting Si—Si bond-bearing compound is a disilane having the general formula (2):

$$R^1R^2R^3Si\text{—}SiR^1R^2R^3 \qquad (2)$$

wherein R$^1$, R$^2$ and R$^3$ are as defined above.

14. The process of claim 13, wherein R$^1$, R$^2$ and R$^3$ are monovalent organic groups which are independently selected from the class consisting of halo-substituted or unsubstituted alkyl, cycloalkyl, aryl, heterocyclic, aralkyl, alkoxy, aryloxy, alkenyl, alkynyl, ferrocenyl groups, and siloxane residues.

15. The process of claim 12, wherein the iron complex is $(C_5H_5)Fe(CO)_2CH_3$, $(C_5H_5)Fe(CO)_2Si(CH_3)_3$, or $[C_5(CH_3)_5]Fe(CO)_2CH_3$.

16. The process of claim 12, wherein the organic solvent is a nitrogen-containing organic compound.

17. The process of claim 12, wherein the step of irradiating with radiation or heating includes irradiating with electromagnetic wave having a shorter wavelength than the visible light or heating at a temperature of 50 to 150° C., or both, for causing the Si—H group-bearing silicon compound to react.

\* \* \* \* \*